(12) United States Patent  
Fei et al.

(10) Patent No.: US 8,283,347 B2  
(45) Date of Patent: Oct. 9, 2012

(54) REDOX MOLECULES AND METHODS OF MAKING THE SAME

(75) Inventors: Jiangfeng Fei, White Plains, NY (US); William Chiang, Pennington, NJ (US); Frank Kerrigan, Wadebridge (GB); Stuart Green, Camelford (GB)

(73) Assignee: Bayer HealthCare LLC, Tarrytown, NY (US)

( * ) Notice: Subject to any disclaimer, the term of this patent is extended or adjusted under 35 U.S.C. 154(b) by 158 days.

(21) Appl. No.: 12/790,165

(22) Filed: May 28, 2010

(65) Prior Publication Data

US 2010/0300896 A1 Dec. 2, 2010

Related U.S. Application Data

(60) Provisional application No. 61/182,906, filed on Jun. 1, 2009.

(51) Int. Cl.  
*C07D 279/18* (2006.01)  
*A61K 31/5415* (2006.01)

(52) U.S. Cl. ...................... 514/226.2; 544/37

(58) Field of Classification Search .................. 544/37; 514/226.2

See application file for complete search history.

(56) References Cited

U.S. PATENT DOCUMENTS

| | | | |
|---|---|---|---|
| 4,490,464 A | 12/1984 | Gorton et al. | |
| 4,710,570 A | 12/1987 | Thien | |
| 4,810,636 A | 3/1989 | Corey | |
| 5,089,112 A | 2/1992 | Skotheim et al. | |
| 5,264,092 A | 11/1993 | Skotheim et al. | |
| 5,393,615 A | 2/1995 | Corey et al. | |
| 5,498,542 A | 3/1996 | Corey et al. | |
| 5,520,786 A | 5/1996 | Bloczynski et al. | |
| 5,631,371 A | 5/1997 | Bloczynski | |
| 6,605,200 B1 | 8/2003 | Mao et al. | |
| 7,163,616 B2 | 1/2007 | Vreeke et al. | |

FOREIGN PATENT DOCUMENTS

EP 1293574 3/2003

OTHER PUBLICATIONS

International Searching Authority, "International Search Report and Written Opinion for PCT/US2010/036591", Dec. 3, 2010, Publisher: European Patent Office, Published in: EPO.
Chemical Abstracts Service, "Chemical Structure Search", Jul. 7, 2008, pp. 1-86, Publisher: American Chemical Society, Published in: Columbus, Ohio, United States.
Chemical Abstracts Service, "Chemical Structure Search", Jul. 7, 2008, pp. 1-214, Publisher: American Chemical Society, Published in: Columbus, Ohio, United States.
Chemical Abstracts Service, "Chemical Structure Search", Aug. 5, 2008, pp. 1-75, Publisher: American Chemical Society, Published in: Columbus, Ohio, United States.

*Primary Examiner* — Kahsay T Habte  
(74) *Attorney, Agent, or Firm* — Blanchard & Associates

(57) ABSTRACT

A non-leaching mediator may include a compound having the general formula (I):

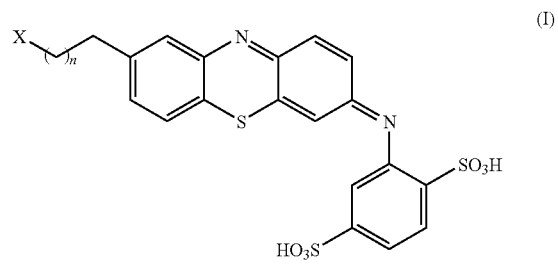

and salts thereof, where n is about 9, and X is a halogen; a compound having the general formula (II):

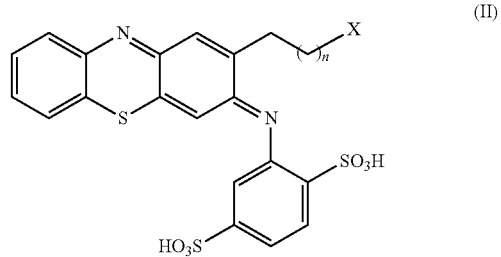

and salts thereof, where n is about 9, and X is a halogen; and/or a compound, having the general formula (III):

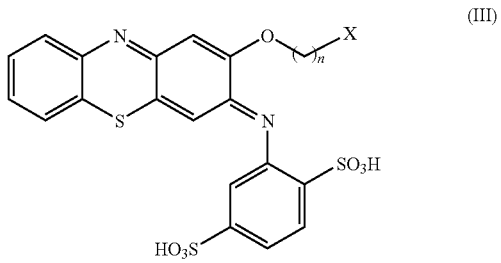

and salts thereof, where n is about 8, and X is a halogen.

14 Claims, 8 Drawing Sheets

REDOX MOLECULES AND METHODS OF MAKING THE SAME

REFERENCE TO RELATED APPLICATIONS

This application claims the benefit of U.S. Provisional Application No. 61/182,906 entitled "Redox Molecules And Methods Of Making The Same" filed Jun. 1, 2009, which is incorporated by reference in its entirety.

BACKGROUND

Biosensors usually analyze a sample of a biological fluid, such as whole blood, urine, or saliva. Samples are compositions that may contain an unknown amount of analyte. Typically, a sample is in liquid form and is an aqueous mixture. A sample may be a derivative of a biological sample, such as an extract, a dilution, a filtrate, or a reconstituted precipitate. A biosensor usually determines the concentration of one or more analytes, a substance present in the sample, such as ketones, glucose, uric acid, lactate, cholesterol, or bilirubin. An analysis determines the presence and/or concentration of the analyte in the sample. The analysis is useful in the diagnosis and treatment of physiological abnormalities. For example, a diabetic individual may use a biosensor to determine the glucose level in blood for adjustments to diet and/or medication.

A biological fluid may be obtained using a variety of methods. In one example of an invasive method, a lancet is used to pierce a user's skin to draw a biological fluid sample, such as blood. This sample is then analyzed with a biosensor external to the skin to determine the concentration of an analyte, such as glucose, in the sample. One disadvantage of this method is that the user's skin must be pierced each time an analyte concentration reading is desired.

One alternative to such an invasive method is to implant a biosensor under the user's skin. This method can allow for multiple analyte concentration readings to be obtained without making a new puncture in the skin for each reading. In addition, the analyte concentration may be monitored at regular intervals without any action required by the user. Thus, implantable biosensors may offer improvements in user compliance and in the amount of information provided.

Many biosensors measure an electrical signal to determine the analyte concentration in a sample of the biological fluid. The analyte typically undergoes an oxidation/reduction (redox) reaction when an excitation signal is applied to the sample. A redox reaction includes oxidation and reduction half-cells. The oxidation half-cell of the reaction involves the loss of at least one electron by the first species. The reduction half-cell involves the addition of at least one electron to the second species. The ionic charge of a species that is oxidized is made more positive by an amount equal to the number of electrons removed. Likewise, the ionic charge of a species that is reduced is made less positive by an amount equal to the number of electrons gained.

In electrochemical sensor systems, a test excitation signal initiates the redox reaction of the analyte in the sample of the biological fluid. The test excitation signal usually is an electrical signal, such as a current or potential, and may be constant, variable, or a combination thereof such as when an AC signal is applied with a DC signal offset. The test excitation signal may be applied as a single pulse or in multiple pulses, sequences, or cycles. The redox reaction generates a test output signal in response to the excitation signal. The output signal usually is another electrical signal, such as a current or potential, which may be measured and correlated with the concentration of the analyte in the sample. The output signal may be measured constantly or periodically during transient and/or steady-state output. Various electrochemical processes may be used such as amperometry, coulometry, voltammetry, gated amperometry, gated voltammetry, and the like.

An enzyme or similar species may be used to enhance the redox reaction of the analyte. The enzyme may be an analyte specific enzyme, such as glucose oxidase or glucose dehydrogenase, which catalyze the oxidation of glucose in a whole blood sample.

A mediator may be used to maintain the oxidation state of the enzyme. A mediator is a substance that may be oxidized or reduced and that may transfer one or more electrons. A mediator is a reagent and is not the analyte of interest, but provides for the indirect measurement of the analyte. More simply, the mediator undergoes a redox reaction in response to the oxidation or reduction of the analyte. The oxidized or reduced mediator then undergoes the opposite reaction at an electrode and is regenerated to its original oxidation number.

The mediator in an electrochemical biosensor may be a one electron transfer mediator or a multi-electron transfer mediator. One electron transfer mediators are chemical moieties capable of taking on one additional electron during the conditions of the electrochemical reaction. One electron transfer mediators include compounds, such as 1,1'-dimethyl ferrocene, ferrocyanide and ferricyanide, and ruthenium(III) and ruthenium(II) hexaamine. Multi-electron transfer mediators are chemical moieties capable of taking on more than one electron during the conditions of the reaction. Multi-electron transfer mediators include two electron transfer mediators, such as the organic quinones and hydroquinones, including phenanthroline quinone; phenothiazine and phenoxazine derivatives; 3-(phenylamino)-3H-phenoxazines; phenothiazines; and 7-hydroxy-9,9-dimethyl-9H-acridin-2-one and its derivatives. Two electron transfer mediators also include the electro-active organic molecules described in U.S. Pat. Nos. 5,393,615; 5,498,542; and 5,520,786.

Two electron mediators may have redox potentials that are at least 100 mV lower, more preferably at least 150 mV lower, than ferricyanide. Two electron transfer mediators include 3-phenylimino-3H-phenothiazines (PIPT) and 3-phenylimino-3H-phenoxazines (PIPO). Two electron mediators also include the carboxylic acid or salt, such as ammonium salts, of phenothiazine derivatives. Two electron mediators further include (E)-2-(3H-phenothiazine-3-ylideneamino) benzene-1,4-disulfonic acid (Structure A), (E)-5-(3H-phenothiazine-3-ylideneamino)isophthalic acid (Structure B), ammonium (E)-3-(3H-phenothiazine-3-ylideneamino)-5-carboxybenzoate (Structure C), and combinations thereof. The structural formulas of these mediators are presented below. While only the di-acid form of the Structure A mediator is shown, mono- and di-alkali metal salts of the acid are included. The sodium salt of the acid may be used for the Structure A mediator. Alkali-metal salts of the Structure B mediator also may be used.

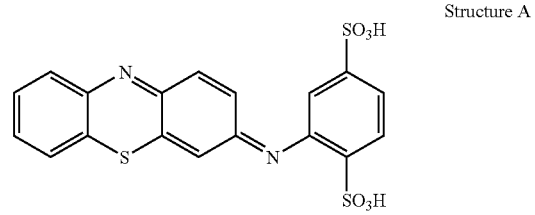

Structure A

Structure B

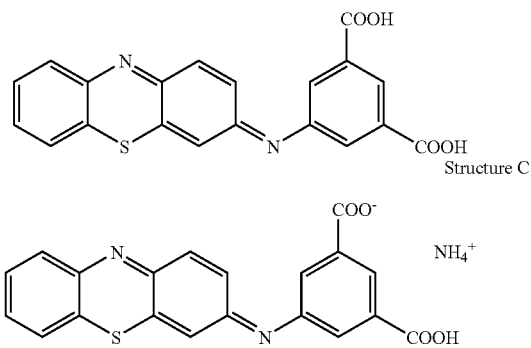

Structure C

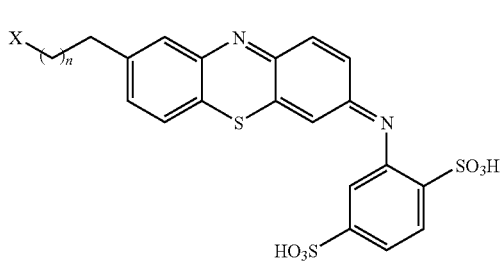

One drawback to the use of implantable electrochemical biosensors is that one or more of the reagents of the biosensor may be released into the biological sample during the analysis. Thus, one or more of the reagents, such as a mediator, may leach from the biosensor into the bodily fluid of the user. Leaching of reagents from the biosensor over time can result in decreased accuracy of the readings obtained from the biosensor. In addition, the reagents may cause undesirable physiological effects if they are released into the patient at a level or rate that is too large.

Accordingly, it would be desirable to have reagents for electrochemical biosensors that do not substantially leach into the biological fluid of the patient. Preferably such non-leaching mediators would be effective in transferring electrons between the analyte and the electrodes and/or in maintaining the oxidation state of the enzyme.

SUMMARY

In one aspect, the invention provides a compound, having the general formula (I):

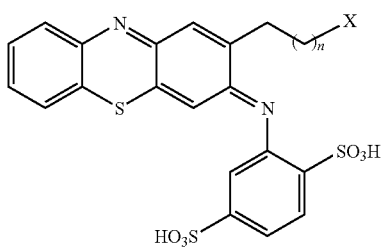

(I)

and salts thereof. In formula (I), n is about 9, and X is a halogen.

In another aspect, the invention provides a compound, having the general formula (II):

(II)

and salts thereof. In formula (II), n is about 9, and X is a halogen.

In another aspect, the invention provides a compound, having the general formula (III):

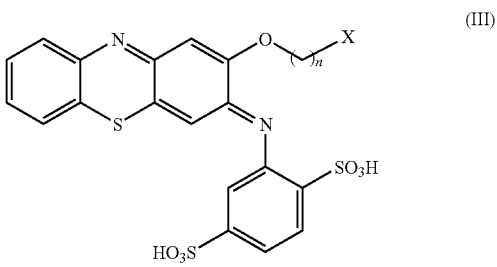

(III)

and salts thereof. In formula (III), n is about 8, and X is a halogen.

In another aspect, the invention provides method of making a composition including at least one compound having the general formula (I) and a compound having the general formula (II), the method including forming a ω-haloalkyl acetate from an α-hydroxyl-ω-haloalkane and acetic anhydride; forming a (ω-acetoxyalkyl)triphenylphosphonium bromide from the ω-haloalkyl acetate and triphenyl phosphine; forming a ω-(4-chloro-3-nitrophenyl)alk-ψ-enyl acetate from the (ω-acetoxyalkyl)triphenylphosphonium bromide, 4-chloro-3-nitrobenzaldehyde and a base; forming a ω-(4-(2-bromophenylthio)-3-nitrophenyl)alk-ψ-enyl acetate from the ω-(4-chloro-3-nitrophenyl)alk-ψ-enyl acetate, 2-bromobenzenethiol and a base; forming a ω-(3-amino-4-(2-bromophenylthio)phenyl)alk-ψ-enyl acetate from the ω-(4-(2-bromophenylthio)-3-nitrophenyl)alk-ψ-enyl acetate, iron and ammonium chloride; forming a ω-(ωH-phenothiazin-2-yl)alk-ψ-enyl acetate from the ω-(3-amino-4-(2-bromophenylthio)phenyl)alk-ψ-enyl acetate, copper iodide, copper and a base; forming a ω-(ωH-phenothiazin-2-yl)alkyl acetate from the ω-(ωH-phenothiazin-2-yl)alk-ψ-enyl acetate, molecular hydrogen and palladium-carbon; forming a ω-(ωH-phenothiazin-2-yl)alkan-α-ol from the ω-(ωH-phenothiazin-2-yl)alkyl acetate, an alcohol and an acid; forming a 2-(ω-haloalkyl)-ωH-phenothiazine from the ω-(ωH-phenothiazin-2-yl)alkan-α-ol, carbon tetrahalide and triphenyl phosphine; and forming a mixture of 2-(8-(ω-haloalkyl)-3H-phenothiazin-3-ylideneamino)benzene-1,4-disulfonic acid and 2-(2-(ω-haloalkyl)-3H-phenothiazin-3-ylideneamino) benzene-1,4-disulfonic acid from the 2-(ω-haloalkyl)-ωH-phenothiazine and $Na_2S_2O_8$.

In another aspect, the invention provides a method of making a compound having the general formula (III), the method including forming 10,10a-dihydro-3H-phenothiazin-8-ol from 8-methoxy-10,10a-dihydro-3H-phenothiazine and an acid; forming a 8-(8-haloalkoxy)-10,10a-dihydro-3H-phenothiazine from 10,10a-dihydro-3H-phenothiazin-8-ol, a α,ω-dihaloalkane and a base; and forming a 2-(2-(8-haloalkoxy)-3H-phenothiazin-3-ylideneamino)benzene-1,4-disulfonic acid from 8-(8-haloalkoxy)-10,10a-dihydro-3H-phenothiazine, 2-aminobenzene-1,4-disulfonic acid, $Na_2S_2O_8$ and a base.

The scope of the present invention is defined solely by the appended claims and is not affected by the statements within this summary.

BRIEF DESCRIPTION OF THE DRAWINGS

The invention can be better understood with reference to the following drawings and description. The components in the figures are not necessarily to scale and are not intended to accurately represent molecules or their interactions, emphasis instead being placed upon illustrating the principles of the invention. Moreover, in the figures, like referenced numerals designate corresponding parts throughout the different views.

DETAILED DESCRIPTION

A non-leaching mediator includes a compound or a mixture of compounds that is not substantially released into a biological sample, but that may be oxidized or reduced, and may transfer one or more electrons from the sample to an electrode of a biosensor. The non-leaching mediator has sufficient solubility in the sample to provide for the indirect measurement of the analyte, undergoing a redox reaction in response to the oxidation or reduction of the analyte. The oxidized or reduced mediator responsive to the analyte concentration of the sample then undergoes the opposite redox reaction at the working electrode of the biosensor and is regenerated to its original oxidation number. A measuring device may correlate the electrons flowing through the working electrode with the analyte concentration of the sample A non-leaching mediator compound may have the general formula (I):

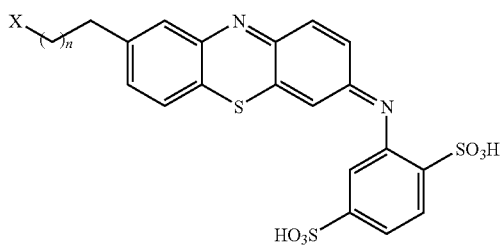

and salts thereof, where n is about 9, X is a halogen, and X is preferably bromine.

The term "salts thereof" means a compound in which the —H atoms of one or both of the —SO$_3$H groups is replaced with a cation independently selected from the group consisting of alkali metal ions, alkaline earth metal ions and ammonium ions. The term "halogen" means —F, —Cl, —Br or —I.

A non-leaching mediator compound may have the general formula (II):

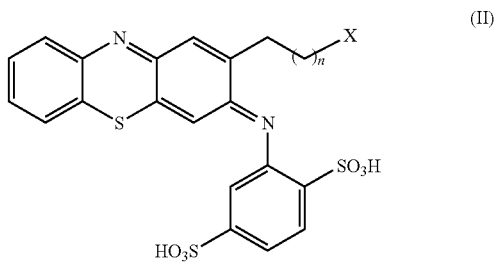

and salts thereof, where n is about 9, X is a halogen, and X is preferably bromine.

A non-leaching mediator composition may include a mixture of a first compound having the general formula (I) and salts thereof, and a second compound having the general formula (II) and salts thereof, where X is preferably bromine.

Figure 1A:
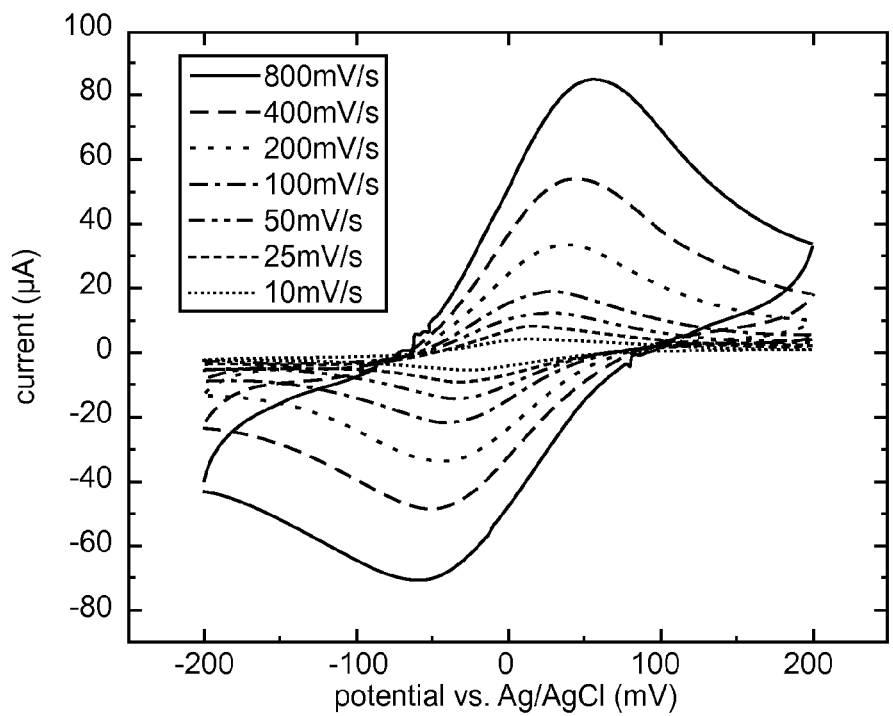
FIGS. 1A and 1B depict graphs illustrating output currents from mediator reduction in response to an input potential.
Figure 1B:
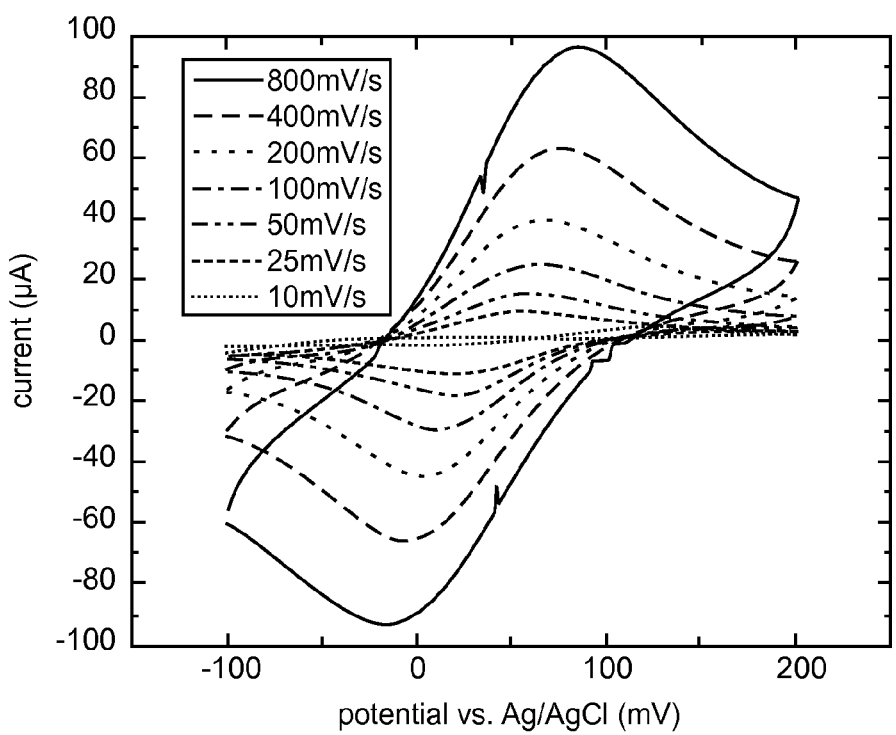

FIGS. 1A and 1B depict graphs illustrating output currents from mediator reduction in response to an input potential. The mediator was a composition including a 3:2 molar mixture of a first compound having the general formula (I), and a second compound having the general formula (II), where X is bromine and each compound is present as the disodium salt. A 5 mm glassy carbon electrode served as a working electrode (WE), Ag/AgCl as a reference electrode (RE), and platinum gauze as a counter electrode (CE). In FIG. 1A, the mediator composition was present at a concentration of 1 mg/mL in a mixture containing 10 mM PBS buffer (pH 7.4), and the input potential was scanned between −200 mV and 200 mV vs. Ag/AgCl. In FIG. 1B, the mediator composition was present at a concentration of 1 mg/mL in a mixture containing 100 mM PBS (pH 7.0) and 100 mM NaCl buffer solution, and the input potential was scanned between −100 mV and 200 mV vs. Ag/AgCl. The rate of change of the input potential was varied from 10 mV/s to 800 mV/s, as indicated in FIGS. 1A and 1B. Referring to FIG. 1B, when the scan rate was less than 50 mV/s, the oxidative and reductive peak separation was around 30-40 mV. This separation indicates that the reduction of this composition was a two-electron process, which is close to the theoretical limit of Nernstian behavior at 60 mV/2e.

The redox potential of the mediator composition of FIGS. 1A and 1B was about −3 mV vs. Ag/AgCl in the 10 mM PBS buffer (pH 7.4), and was about 40 mV vs. Ag/AgCl in the mixture of 100 mM PBS (pH 7.0) and 100 mM NaCl buffer. These redox potentials are similar to that of the conventional mediator (E)-2-(3H-phenothiazine-3-ylideneamino)benzene-1,4-disulfonic acid (Structure A), which is −50 mV vs. Ag/AgCl.

The open circuit voltage between the WE and the RE also was measured for the mediator composition of FIGS. 1A and 1B. The open circuit voltage is a measure of the redox state of the mediator. The open circuit voltage of the mixture was 59 mV vs. Ag/AgCl in the 10 mM PBS buffer, which suggests that the mediator was in its oxidized state after synthesis.

Figure 2:
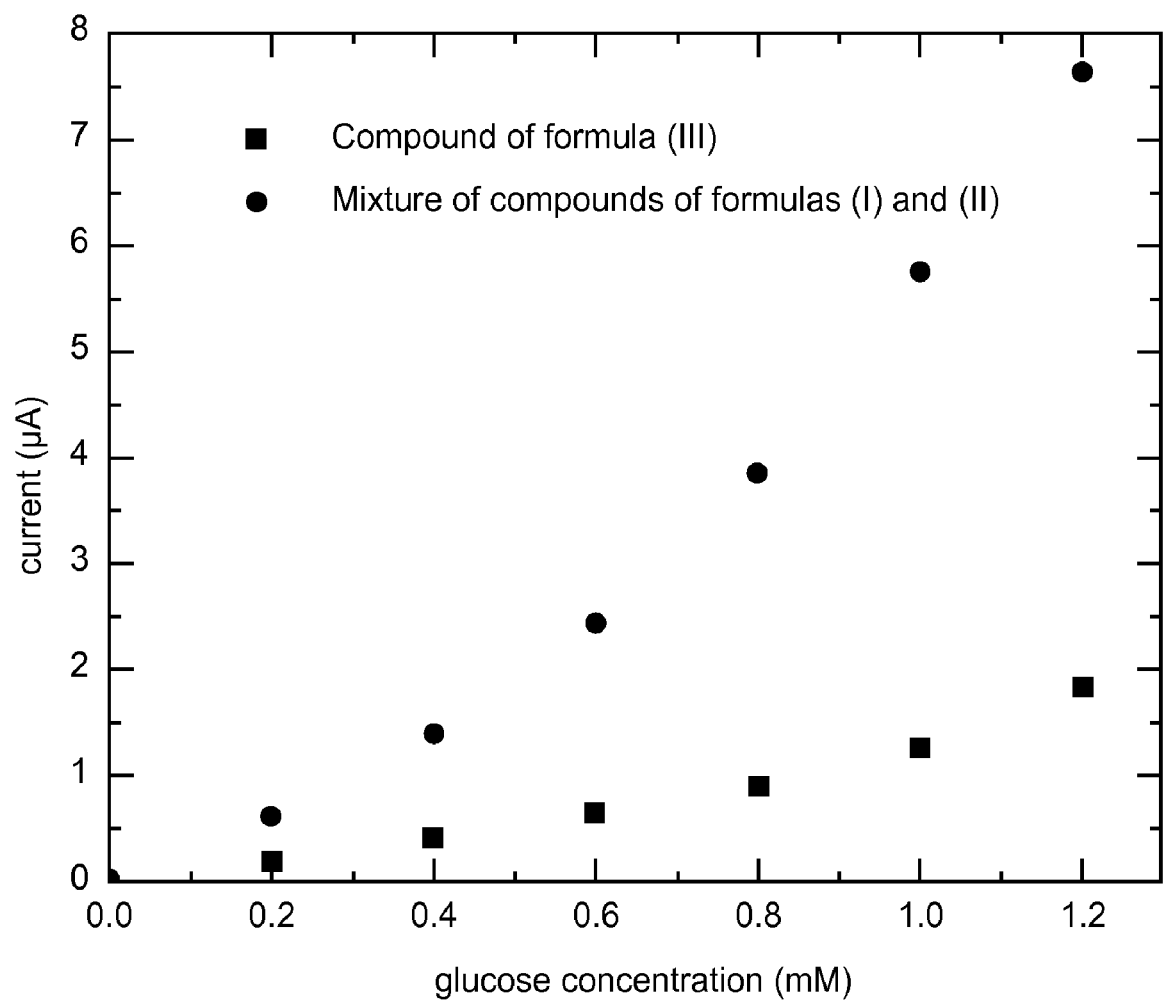
FIG. 2 depicts a graph illustrating output currents from mediator reduction in response to an input potential when the mediator is in a mixture containing glucose and glucose dehydrogenase.

FIG. 2 depicts a graph illustrating output currents from mediator oxidation in response to an input potential when the mediator is in a mixture containing glucose and glucose dehydrogenase. The mediator was the composition used in FIGS. 1A and 1B. A 5 mm glassy carbon electrode served as a WE, Ag/AgCl as a RE, and platinum gauze as a CE. The composition was present at a concentration of 2 mg/mL in a mixture containing 10 mM PBS buffer (pH 7.4), and the input potential was 100 mV vs. Ag/AgCl. The output current increased as the glucose concentration increased from 0 to 1.2 mM in the mixture. Thus, the composition may be used as a mediator for the redox reaction correlating the glucose concentration in a sample with an electrical signal.

Figure 3:
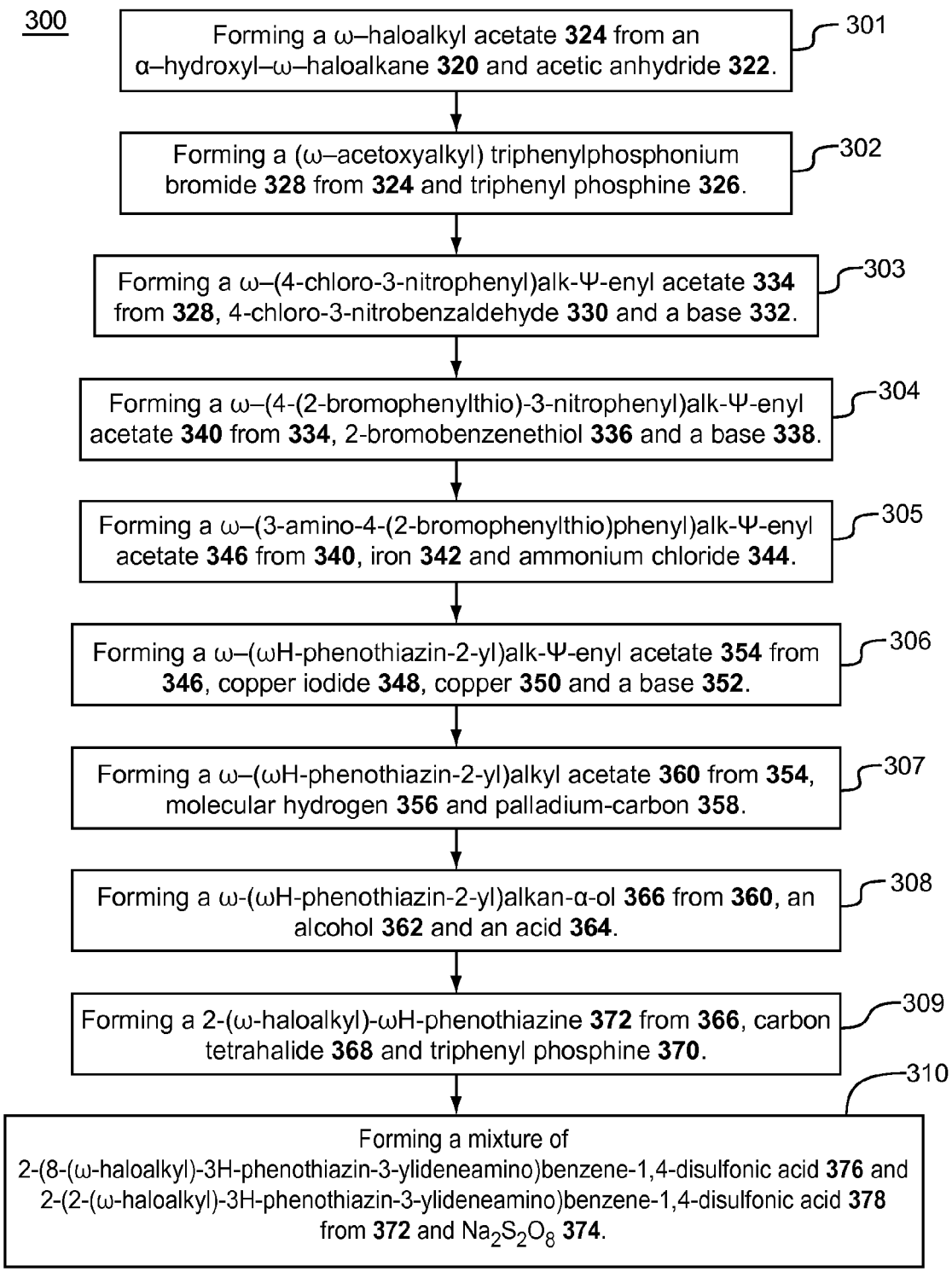
FIG. 3 depicts a method for making a composition including at least one compound having the general formula (I) or (II).

FIG. 3 depicts a method 300 of making a composition including at least one compound having the general formula (I) or (II) and salts thereof. The method 300 includes forming 301 a ω-haloalkyl acetate 324 from an α-hydroxyl-ω-haloalkane 320 and acetic anhydride 322; forming 302 a (ω-acetoxyalkyl)triphenylphosphonium bromide 328 from the ω-haloalkyl acetate 324 and triphenyl phosphine 326; forming 303 a ω-(4-chloro-3-nitrophenyl)alk-ψ-enyl acetate 334 from the (ω-acetoxyalkyl) triphenylphosphonium bromide 328, 4-chloro-3-nitrobenzaldehyde 330 and a base 332; forming 304 a ω-(4-(2-bromophenylthio)-3-nitrophenyl)alk-ω-enyl acetate 340 from the ω-(4-chloro-3-nitrophenyl)alk-ψ-enyl acetate 334, 2-bromobenzenethiol 336 and a base 338; forming 305 a ω-(3-amino-4-(2-bromophenylthio)phenyl) alk-ψ-enyl acetate 346 from the ω-(4-(2-bromophenylthio)-3-nitrophenyl)alk-ψ-enyl acetate 340, iron 342 and ammonium chloride 344; forming 306 a ω(ωH-phenothiazin-2-yl)alk-ψ-enyl acetate 354 from the ω-(3-amino-4-(2-bromophenylthio)phenyl)alk-ψ-enyl acetate 346, copper iodide 348, copper 350 and a base 352; forming 307 a ω-(ωH-phenothiazin-2-yl)alkyl acetate 360 from the ω-(ωH-phenothiazin-2-yl)alk-ψ-enyl acetate 354, molecular hydrogen 356 and palladium-carbon 358; forming 308 a ω-(ωH-phenothiazin-2-yl)alkan-α-ol 366 from the ω-(ωH-phenothiazin-2-yl)alkyl acetate 360, an alcohol 362 and an acid 364; forming 309 a 2-(ω-haloalkyl)-ωH-phenothiazine 372 from the ω-(ωH-phenothiazin-2-yl)alkan-α-ol 366, carbon tetrahalide 368 and triphenyl phosphine 370; and forming 310 a mixture of 2-(8-(ω-haloalkyl)-3H-phenothiazin-3-ylideneamino)benzene-1,4-disulfonic acid 376 and 2-(2-(ω-haloalkyl)-3H-phenothiazin-3-ylideneamino)benzene-1,4-disulfonic acid 378 from the 2-(ω-haloalkyl)-ωH-phenothiazine 372 and Na$_2$S$_2$O$_8$ 374.

Figure 4:
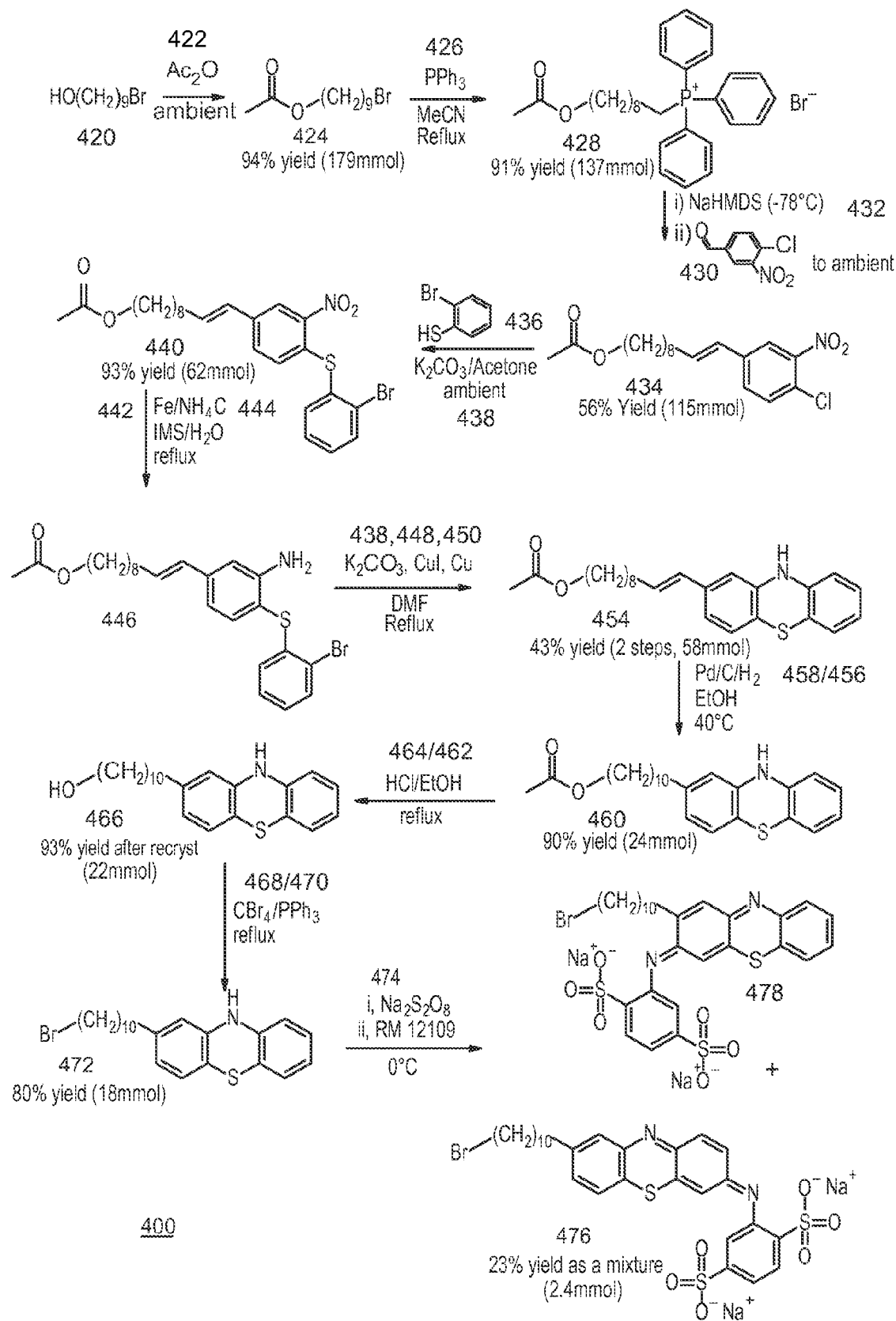
FIG. 4 depicts chemical structures, reaction schemes and product yields for a method of making a composition including a mixture of a first compound having the general formula (I), and a second compound having the general formula (II), where X is bromine and each compound is present as the disodium salt.

FIG. 4 depicts chemical structures, reaction schemes and product yields for a method 400 of making a composition including a mixture of a first compound having the general formula (I), and a second compound having the general formula (II), where X is bromine and each compound is present as the disodium salt. Method 400 includes forming 9-bromononyl acetate 424 from 9-halononan-1-ol 420 and acetic anhydride 422; forming (9-acetoxynonyl)triphenylphosphonium 428 from 9-bromononyl acetate 424 and triphenyl phosphine 426; forming 10-(4-chloro-3-nitrophenyl)dec-9-enyl acetate 434 from (9-acetoxynonyl)triphenylphosphonium 428, 4-chloro-3-nitrobenzaldehyde 430 and sodium bis(trimethylsilyl)amide(NaHMDS) 432; forming 10-(4-(2-bromophenylthio)-3-nitrophenyl)dec-9-enyl acetate 440 from 10-(4-chloro-3-nitrophenyl)dec-9-enyl acetate 434, 2-bromobenzenethiol 436 and K$_2$CO$_3$ 438; forming 10-(3-amino-4-(2-bromophenylthio)phenyl)dec-9-enyl acetate 446 from 10-(4-(2-bromophenylthio)-3-nitrophenyl)dec-9-enyl acetate 440, iron 442 and ammonium chloride 444; forming 10-(10H-phenothiazin-2-yl)dec-9-enyl acetate 454 from 10-(3-amino-4-(2-bromophenylthio)phenyl)dec-9-enyl acetate 446, copper iodide 448, copper 450 and K$_2$CO$_3$ 438; forming 10-(10H-phenothiazin-2-yl)decyl acetate 460 from 10-(10H-phenothiazin-2-yl)dec-9-enyl acetate 454, molecular hydrogen 456 and palladium-carbon 458; forming 10-(10H-phenothiazin-2-yl)decan-1-ol 466 from 10-(10H-phenothiazin-2-yl)decyl acetate 460, ethanol 462 and HCl 464; forming 2-(10-bromodecyl)-10H-phenothiazine 472 from 10-(10H-phenothiazin-2-yl)decan-1-ol 466, carbon tetrabromide 468 and triphenyl phosphine 470; and forming a mixture of 2-(8-(10-bromodecyl)-3H-phenothiazin-3-ylideneamino)benzene-1,4-disulfonic acid 476 and 2-(2-(10-bromodecyl)-3H-phenothiazin-3-ylideneamino)benzene-1,4-disulfonic acid 478 from the 2-(10-bromodecyl)-10H-phenothiazine 472 and Na$_2$S$_2$O$_8$ 474.

A non-leaching mediator compound may have the general formula (III):

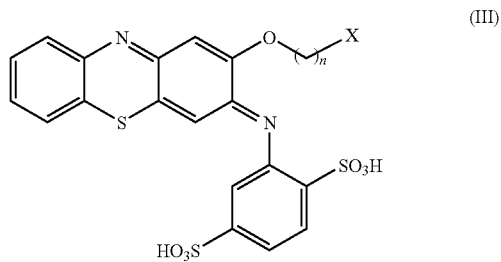

and salts thereof, where n is about 8, X is a halogen, and X is preferably bromine.

Figure 5A:
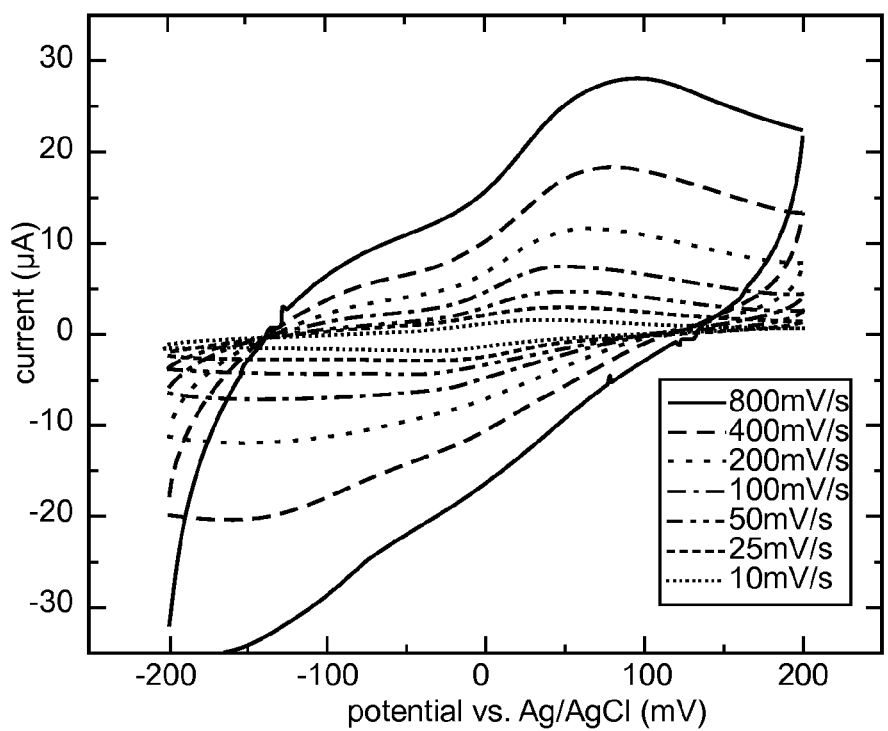
FIGS. 5A and 5B depict graphs illustrating output currents from mediator reduction in response to an input potential.
Figure 5B:
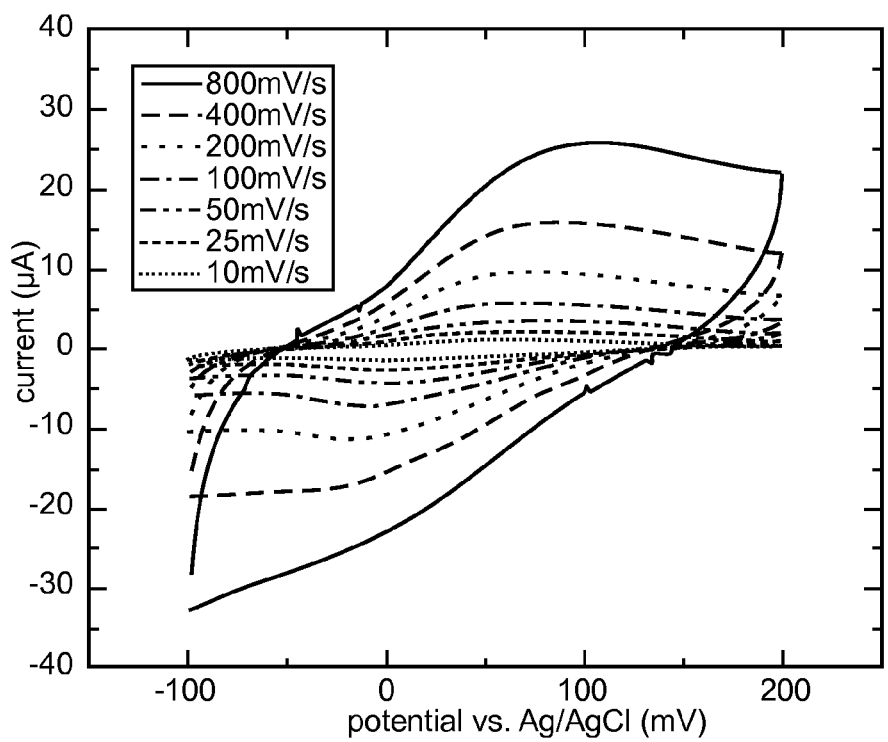

FIG. 5A and FIG. 5B depict graphs illustrating output currents from mediator reduction in response to an input potential. The mediator was a compound having general formula (III), where X is bromine. A 5 mm glassy carbon electrode served as a WE, Ag/AgCl as a RE, and platinum gauze as a CE. In FIG. 5A, the mediator was present at a concentration of 1 mg/mL in a mixture containing 10 mM PBS buffer (pH 7.4), and the input potential was scanned between −200 mV and 200 mV vs. Ag/AgCl. In FIG. 5B, the mediator was present at a concentration of 1 mg/mL in a mixture containing 100 mM PBS (pH 7.0) and 100 mM NaCl buffer solution, and the input potential was scanned between −100 mV and 200 mV vs. Ag/AgCl. The rate of change of the input potential was varied from 10 mV/s to 800 mV/s, as indicated in FIGS. 5A and 5B. Referring to FIG. 5B, when the scan rate was less than 50 mV/s, the oxidative and reductive peak separation was around 30-40 mV. This separation indicates that the reduction of this mediator was a two-electron process, which is close to the theoretical limit of Nernstian behavior at 60 mV/2e.

The redox potential of the compound having general formula (III), where X is bromine, was about 3 mV vs. Ag/AgCl in the 10 mM PBS buffer (pH 7.4), and was about 15 mV vs. Ag/AgCl in the mixture of 100 mM PBS (pH 7.0) and 100 mM NaCl buffer. These redox potentials are similar to that of the conventional mediator (E)-2-(3H-phenothiazine-3-ylideneamino)benzene-1,4-disulfonic acid (Structure A), which is −50 mV vs. Ag/AgCl.

The open circuit voltage between the WE and the RE also was measured for the compound having general formula (III), where X is bromine. The open circuit voltage of the compound was 111 mV vs. Ag/AgCl in the 10 mM PBS buffer, which suggests that the mediator was in its oxidized state after synthesis.

Referring to FIG. 2, a compound having general formula (III), where X is bromine, can be used as a mediator for the redox reaction correlating the glucose concentration of a sample with an electrical signal. A 5 mm glassy carbon electrode served as a WE, Ag/AgCl as a RE, and platinum gauze as a CE. The mediator was present at a concentration of 3 mg/mL in a mixture containing 10 mM PBS buffer (pH 7.4), and the input potential was 100 mV vs. Ag/AgCl. The output current increased as the glucose concentration increased from 0 to 1.2 mM in the mixture. Thus, the composition may be used as a mediator for the redox reaction correlating the glucose concentration in a sample with an electrical signal.

Figure 6:
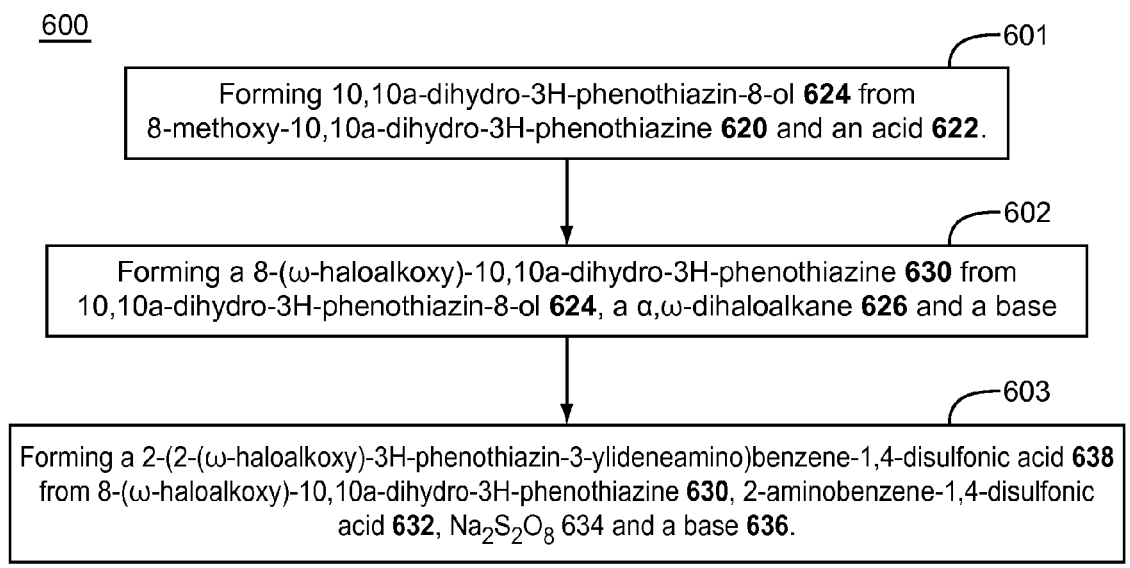
FIG. 6 depicts a method for making a compound having the general formula (III).

FIG. 6 depicts a method 600 of making a compound having the general formula (III) and salts thereof. The method 600 includes forming 601 10,10a-dihydro-3H-phenothiazin-8-ol 624 from 8-methoxy-10,10a-dihydro-3H-phenothiazine 620 and an acid 622; forming 602 a 8-(ω-haloalkoxy)-10,10a-dihydro-3H-phenothiazine 630 from 10,10a-dihydro-3H-phenothiazin-8-ol 624, a α,ω)-dihaloalkane 626 and a base 628; and forming 603 a 2-(2-(ω-haloalkoxy)-3H-phenothiazin-3-ylideneamino)-benzene-1,4-disulfonic acid 638 from 8-(ω-haloalkoxy)-10,10a-dihydro-3H-phenothiazine 630, 2-aminobenzene-1,4-disulfonic acid 632, $Na_2S_2O_8$ 634 and a base 636.

Figure 7:
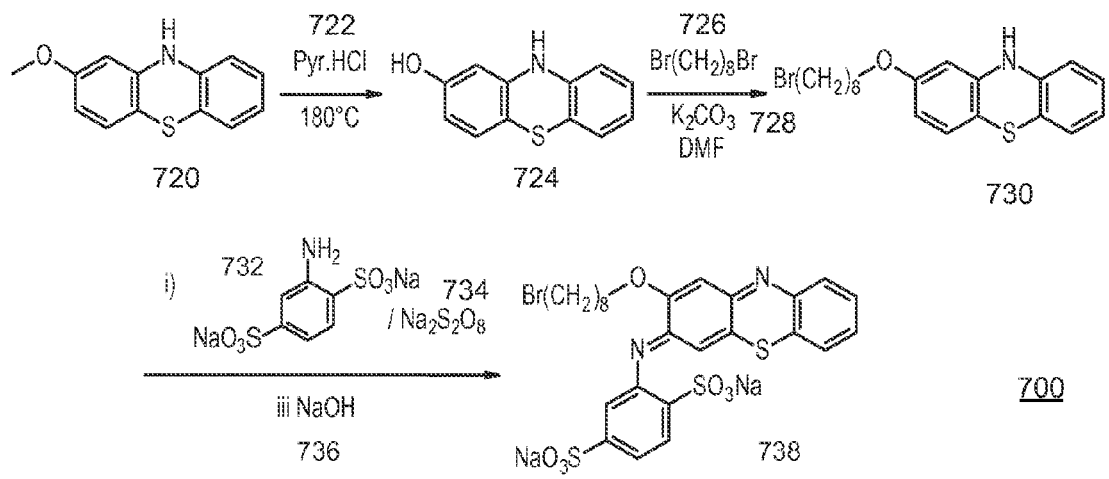
FIG. 7 depicts chemical structures and reaction schemes for a method of making a compound having the general formula (III), where X is bromine and the compound is present as the disodium salt.

FIG. 7 depicts chemical structures and reaction schemes for an example of a method 700 of making a compound having the general formula (III), where X is bromine and the compound is present as the disodium salt. Method 700 includes forming 10,10a-dihydro-3H-phenothiazin-8-ol 724 from 8-methoxy-10,10a-dihydro-3H-phenothiazine 720 and HCl 722; forming 8-(8-bromooctanoxy)-10,10a-dihydro-3H-phenothiazine 730 from 10,10a-dihydro-3H-phenothiazin-8-ol 724, 1,8-dibromooctane 726 and potassium carbonate 728; and forming 2-(2-(8-bromooctanoxy)-3H-phenothiazin-3-ylideneamino)benzene-1,4-disulfonic acid 738 from 8-(8-bromooctanoxy)-10,10a-dihydro-3H-phenothiazine 730, 2-aminobenzene-1,4-disulfonic acid 732, $Na_2S_2O_8$ 734 and sodium hydroxide 736.

Compounds having the general formulas (I), (II) and/or (III) may be useful as polymer bondable mediators. A polymer bondable mediator includes a mediator that can be bonded to a polymer. The terminal halogen group may be reacted with a functional group of a polymer, bonding the mediator to the polymer. Bonding includes covalent bonding where an electron pair is shared between two atoms. The terminal halogen group may be converted into a different functional group, and this modified mediator may then be bound to a polymer. The polymer may be a binder of a reagent composition for an electrochemical biosensor.

Figure 8:
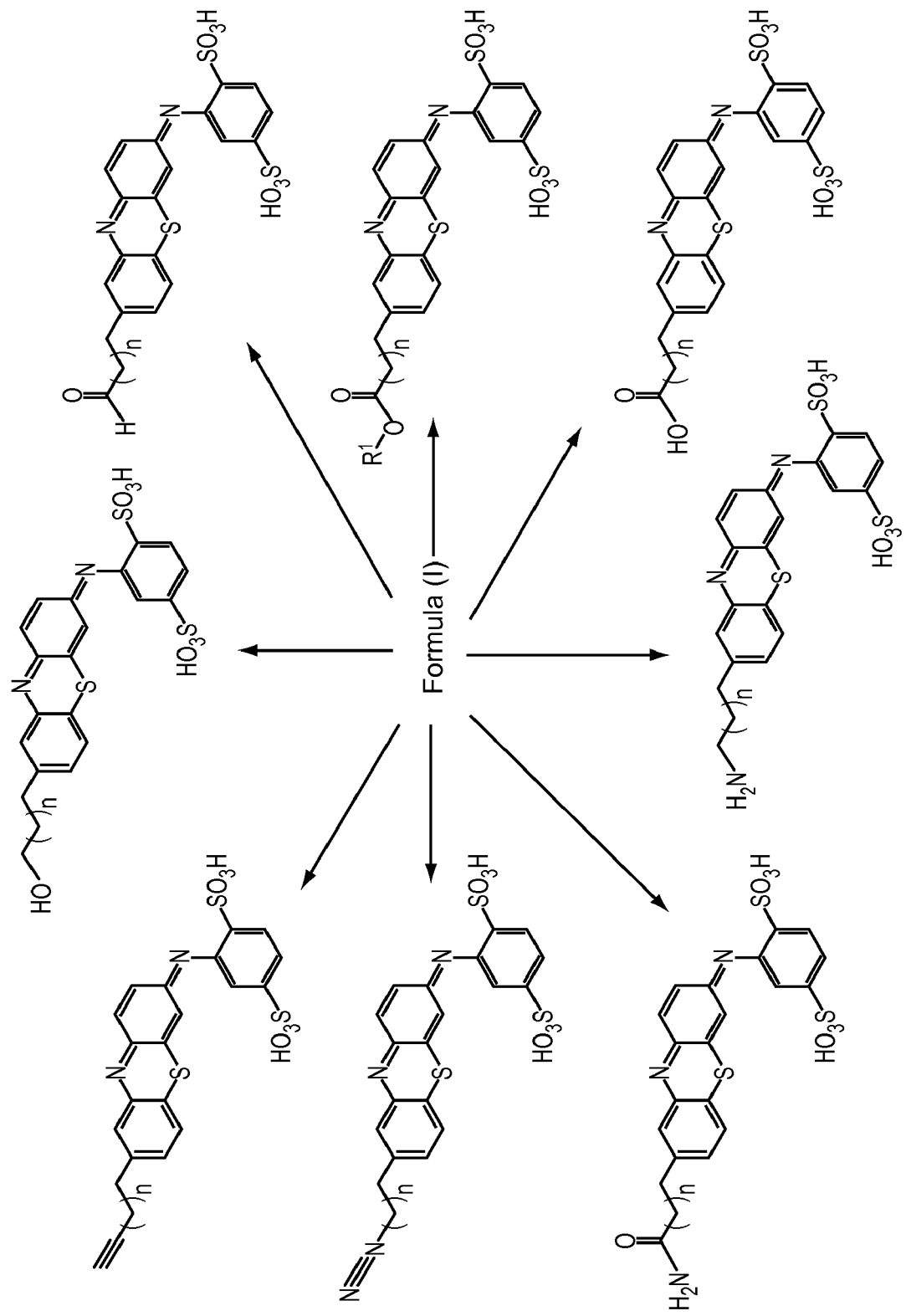
FIG. 8 depicts examples of polymer bondable mediators having terminal functional groups other than halogen.

FIG. 8 depicts examples of polymer bondable mediators having terminal functional groups other than halogen. These examples are based on compounds having the general formula (I); however, similar derivatives of compounds having the general formulas (II) or (III) are envisioned. The exemplary terminal functional groups depicted in FIG. 8 are, clockwise from top, hydroxyl, aldehyde, ester ($R^1$=organic group), carboxylic acid, amine, amide, azide and alkyne groups.

Compounds having the general formulas (I), (II) and/or (III) may be useful as intermediates for preparing polymerizable mediators. A polymerizable mediator includes a mediator that can polymerize to form a polymer, or that can copolymerize with other monomers to form a copolymer. The terminal halogen group may be converted into a functional group capable of polymerization or copolymerization. For example, the terminal halogen may be converted into a carbon-carbon double or triple bond. This modified mediator having a terminal unsaturated group may then polymerize or copolymerize through radical, anionic and/or cationic polymerization. The terminal halogen also may be converted into a functional group that can undergo a condensation reaction. This modified mediator having a terminal functional group may then polymerize or copolymerize through a condensation polymerization. The resulting polymer may be used as a binder of a reagent composition for an electrochemical biosensor.

Figure 9:
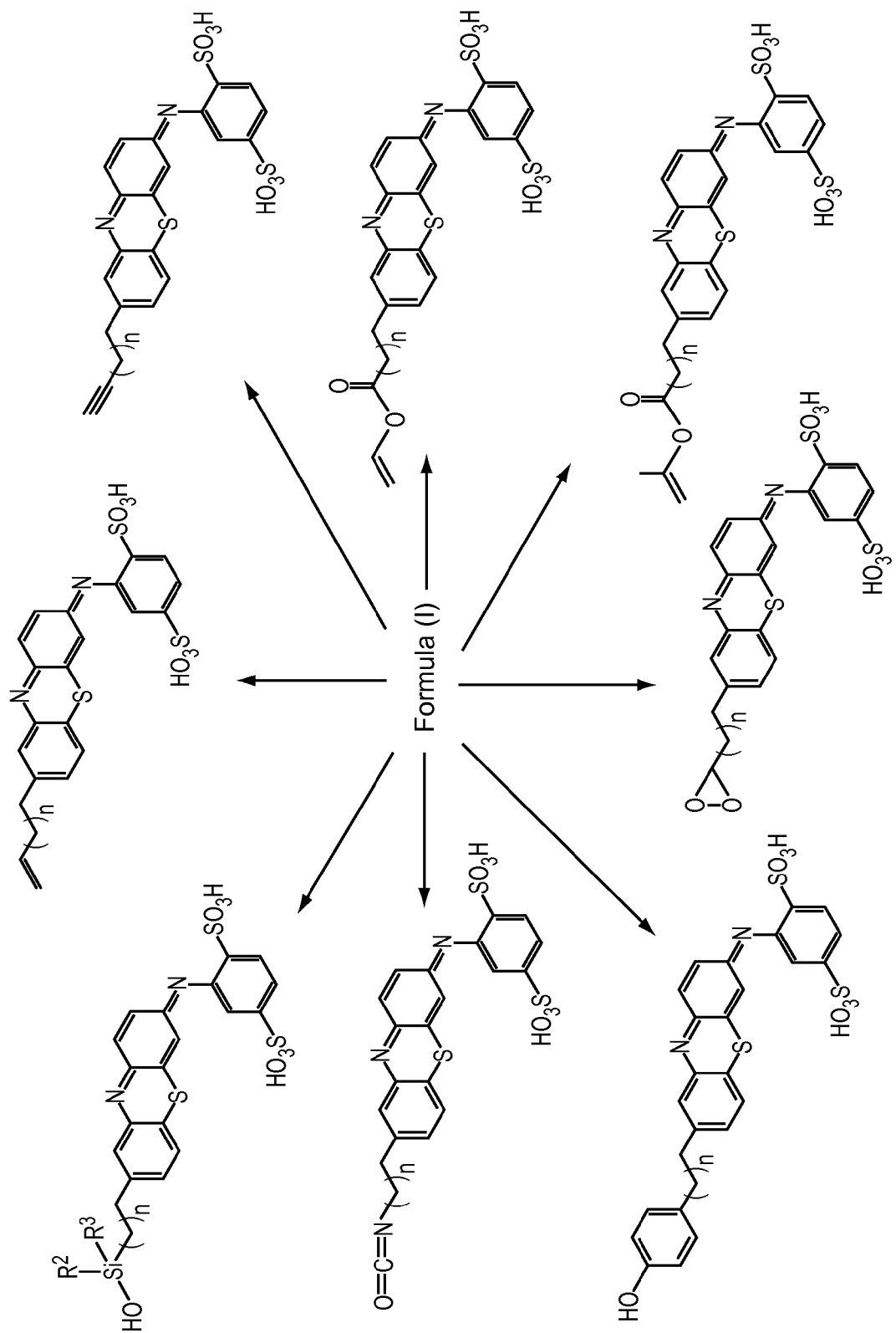
FIG. 9 depicts examples of polymerizable mediators having terminal functional groups other than halogen.

FIG. 9 depicts examples of polymerizable mediators having terminal functional groups other than halogen. These examples are based on compounds having the general formula (I); however, similar derivatives of compounds having the general formulas (II) or (III) are envisioned. The exemplary terminal functional groups depicted in FIG. 9 are, clockwise from top, alkene, alkyne, acrylate, methacrylate, epoxide, phenol, isocyanate and silanol groups ($R^2$, $R^3$=organic groups).

Compounds having the general formulas (I), (II) and/or (III) may be useful as surface active mediators. A surface active mediator is a non-bonded mediator that includes a hydrophobic portion and a hydrophilic portion. For compounds having the general formulas (I), (II) and/or (III), the alkyl chain group may function as the hydrophobic portion, whereas the benzene 1,4-disulfonic acid group may function as the hydrophilic portion. The compounds also may be modified by converting the terminal halogen group into a more hydrophobic group, such as an alkyl group, to further increase the difference in solubility of the two portions of the mediators.

Polymer bondable mediators, polymerizable mediators and/or surface active mediators may be used to provide immobilized mediators for electrochemical bioanalysis. While the benzene 1,4-disulfonic acid group of the compound may be sufficiently solubilized in an aqueous sample to interact with an analyte and/or an enzyme, the alkyl chain group of the compound may have a solubility in the sample that is so low as to inhibit the entire compound from dissolving in the sample. The overall solubility of the mediator may be further diminished when the mediator is bound to a polymer. Thus, compounds having the general formulas (I), (II) and/or (III), and/or derivatives of these compounds bound to a polymer, may be useful as mediators having little or no ability to leach into a sample.

While various embodiments of the invention have been described, it will be apparent to those of ordinary skill in the art that other embodiments and implementations are possible within the scope of the invention. Accordingly, the invention is not to be restricted except in light of the attached claims and their equivalents.

What is claimed is:

1. A compound having formula (I) or salts thereof:

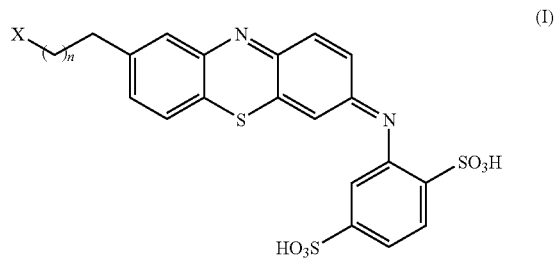

where n is about 9, and X is a halogen.

2. The compound of claim 1, where X is Br.

3. A compound having formula (II) or salts thereof:

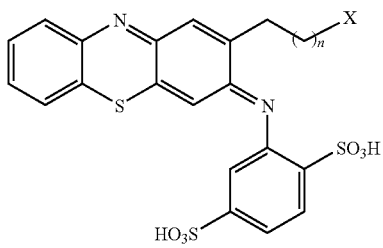

where n is about 9, and X is a halogen.

4. The compound of claim 3, where X is Br.

5. A compound having formula (III) or salts thereof:

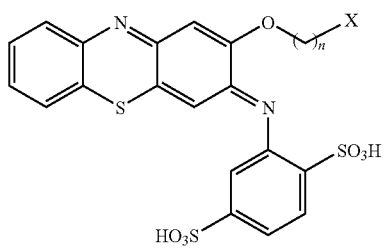

where n is about 8, and X is a halogen.

6. The compound of claim 5, where X is Br.

7. A composition, comprising:
a mixture of a first compound having formula (I) or salts thereof:

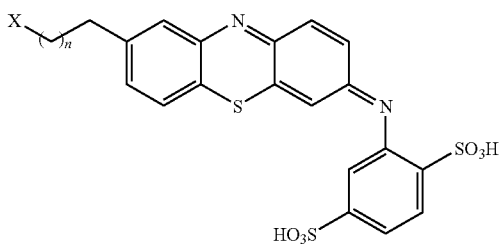

where n is about 9, and X is a halogen; and
a second compound having formula (II) or salts thereof:

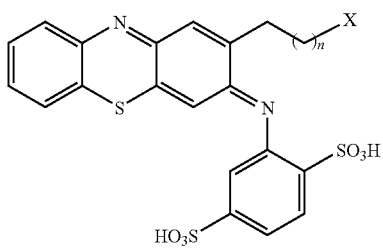

where n is about 9, and X is a halogen.

8. The composition of claim 7, where X is Br.

9. A method of making a composition comprising at least one compound having formula (I) or salts thereof:

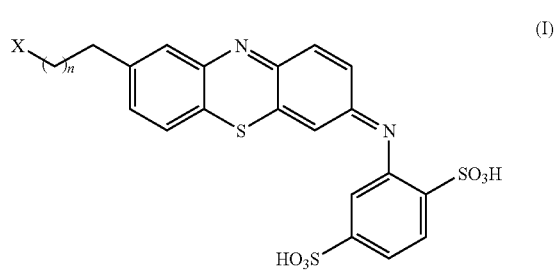

where n is about 9, and X is a halogen, and
a compound having formula (II) or salts thereof:

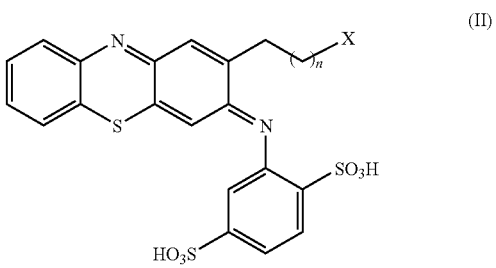

where n is about 9, and X is a halogen;
the method comprising:
forming a ω-haloalkyl acetate from an α-hydroxyl-ω-haloalkane and acetic anhydride;
forming a (ω-acetoxyalkyl)triphenylphosphonium bromide from the ω-haloalkyl acetate and triphenyl phosphine;
forming a ω-(4-chloro-3-nitrophenyl)alk-ψ-enyl acetate from the (ω-acetoxyalkyl)triphenylphosphonium bromide, 4-chloro-3-nitrobenzaldehyde and a base;
forming a ω-(4-(2-bromophenylthio)-3-nitrophenyl)alk-ψ-enyl acetate from the ω-(4-chloro-3-nitrophenyl)alk-ψ-enyl acetate, 2-bromobenzenethiol and a base;
forming a ω-(3-amino-4-(2-bromophenylthio)phenyl)alk-ψ-enyl acetate from the ω-(4-(2-bromophenylthio)-3-nitrophenyl)alk-ψ-enyl acetate, iron and ammonium chloride;
forming a ω-(O)H-phenothiazin-2-yl)alk-ψ-enyl acetate from the ω-(3-amino-4-(2-bromophenylthio)phenyl)alk-ψ-enyl acetate, copper iodide, copper and a base;
forming a ω-(ωH-phenothiazin-2-yl)alkyl acetate from the ω-(ωH-phenothiazin-2-yl)alk-ψ-enyl acetate, molecular hydrogen and palladium-carbon;
forming a ω-(ωH-phenothiazin-2-yl)alkan-α-ol from the ω-(ωH-phenothiazin-2-yl)alkyl acetate, an alcohol and an acid;
forming a 2-(ω-haloalkyl)-ωH-phenothiazine from the ω-(ωH-phenothiazin-2-yl)alkan-α-ol, carbon tetrahalide and triphenyl phosphine; and
forming a mixture of 2-(8-(ω-haloalkyl)-3H-phenothiazin-3-ylideneamino)benzene-1,4-disulfonic acid and 2-(2-(ω-haloalkyl)-3H-phenothiazin-3-ylideneamino)benzene-1,4-disulfonic acid from the 2-(ω-haloalkyl)-ωH-phenothiazine and $Na_2S_2O_8$.

10. The method of claim 9, where
the α-hydroxyl-ω-haloalkane comprises a α-hydroxyl-ω-bromoalkane;
the 2-(8-(ω-haloalkyl)-3H-phenothiazin-3-ylideneamino)benzene-1,4-disulfonic acid comprises a 2-(8-(ω-bromoalkyl)-3H-phenothiazin-3-ylideneamino)benzene-1,4-disulfonic acid; and the 2-(2-(ω-haloalkyl)-3H-phenothiazin-3-ylideneamino)benzene-1,4-disulfonic acid comprises a 2-(2-(ω-bromoalkyl)-3H-phenothiazin-3-ylideneamino)benzene-1,4-disulfonic acid.

11. The method of claim 9, where the α-hydroxyl-ω-haloalkane comprises 9-halononan-1-ol;

the 2-(8-(ω-haloalkyl)-3H-phenothiazin-3-ylideneamino)benzene-1,4-disulfonic acid comprises 2-(8-(10-bromodecyl)-3H-phenothiazin-3-ylideneamino)benzene-1,4-disulfonic acid; and the 2-(2-(ω-haloalkyl)-3H-phenothiazin-3-ylideneamino)benzene-1,4-disulfonic acid comprises 2-(2-(10-bromodecyl)-3H-phenothiazin-3-ylideneamino)benzene-1,4-disulfonic acid.

12. A method of making a compound having formula (III) or salts thereof:

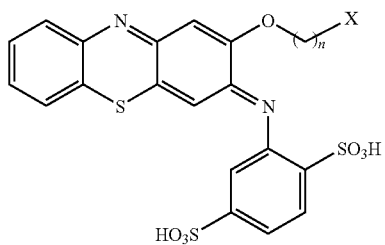

(III)

where n is about 8, and X is a halogen;

the method comprising:

forming 10,10a-dihydro-3H-phenothiazin-8-ol from 8-methoxy-10,10a-dihydro-3H-phenothiazine and an acid;

forming a 8-(ω-haloalkoxy)-10,10a-dihydro-3H-phenothiazine from 10,10a-dihydro-3H-phenothiazin-8-ol, a α,ω-dihaloalkane and a base; and forming a 2-(2-(ω-haloalkoxy)-3H-phenothiazin-3-ylideneamino)benzene-1,4-disulfonic acid from 8-(ω-haloalkoxy)-10,10a-dihydro-3H-phenothiazine, 2-aminobenzene-1,4-disulfonic acid, $Na_2S_2O_8$ and a base.

13. The method of claim 12, where the α,ω-dihaloalkane comprises a α,ω-dibromoalkane; and the 2-(2-(ω-haloalkoxy)-3H-phenothiazin-3-ylideneamino)benzene-1,4-disulfonic acid comprises a 2-(2-(ω-bromoalkoxy)-3H-phenothiazin-3-ylideneamino)benzene-1,4-disulfonic acid.

14. The method of claim 12, where the α,ω-dihaloalkane comprises 1,8-dibromooctane; and the 2-(2-(ω-haloalkoxy)-3H-phenothiazin-3-ylideneamino)benzene-1,4-disulfonic acid comprises 2-(2-(8-bromooctanoxy)-3H-phenothiazin-3-ylideneamino)benzene-1,4-disulfonic acid.

* * * * *